US012561910B2

(12) United States Patent
Osswald et al.

(10) Patent No.: US 12,561,910 B2
(45) Date of Patent: Feb. 24, 2026

(54) AUTOMATIC NEUROSURGICAL TARGET AND ENTRY POINT IDENTIFICATION

(71) Applicant: ClearPoint Neuro, Inc., Solana Beach, CA (US)

(72) Inventors: Christian R. Osswald, Roselle, IL (US); Lyubomir G. Zagorchev, Burlington, MA (US); Timothy N. Orr, Vaughan (CA); Philip B. Hotte, Mississauga (CA)

(73) Assignee: ClearPoint Neuro, Inc., Solana Beach, CA (US)

( * ) Notice: Subject to any disclaimer, the term of this patent is extended or adjusted under 35 U.S.C. 154(b) by 216 days.

(21) Appl. No.: 18/237,885

(22) Filed: Aug. 24, 2023

(65) Prior Publication Data

US 2025/0069332 A1 Feb. 27, 2025

(51) Int. Cl.
*G06T 17/20* (2006.01)
*A61B 34/10* (2016.01)
(Continued)

(52) U.S. Cl.
CPC .............. *G06T 17/20* (2013.01); *A61B 34/10* (2016.02); *G06T 15/04* (2013.01); *G06T 19/20* (2013.01);
(Continued)

(58) Field of Classification Search
None
See application file for complete search history.

(56) References Cited

U.S. PATENT DOCUMENTS

| | | | |
|---|---|---|---|
| 8,532,741 | B2 | 9/2013 | Heruth et al. |
| 2013/0178693 | A1 | 7/2013 | Neuvonen et al. |

(Continued)

FOREIGN PATENT DOCUMENTS

| | | |
|---|---|---|
| JP | 6650913 B2 | 2/2020 |
| WO | 2012092511 A2 | 7/2012 |
| WO | 2020109188 A1 | 6/2020 |

OTHER PUBLICATIONS

Zagorchev et al, "A Curvature-Adaptive Implicit Surface Reconstruction for Irregularly Spaced Points," IEEE Transactions on Visualization and Computer Graphics, vol. 18, No. 9, Sep. 2012, pp. 1460-1473.

*Primary Examiner* — Andrew G Yang
(74) *Attorney, Agent, or Firm* — Sheppard Mullin Richter & Hampton LLP

(57) ABSTRACT

Examples of the presently disclosed technology provide systems and methods for automatically identifying candidate target locations and candidate surgical trajectories using a functional brain activity scan mapped to patient-specific 3D brain structure representations generated from a structural scan of a patient's brain. In an illustrative example, the methods and systems adapt a shape-constrained deformable brain model to a structural scan of a patient's brain to generate a patient-specific 3D brain representation of the patient's brain and extract a patient-specific 3D brain structure representation from the patient-specific 3D brain representation. The functional brain activity of the patient's brain is registered to the structural scan and mapped to the extracted patient-specific 3D brain structure representation from the structural scan. One or more target locations are identified on the patient-specific 3D brain structure representation based on the mapped functional brain activity.

20 Claims, 10 Drawing Sheets

800

ADAPT A SHAPE-CONSTRAINED DEFORMABLE BRAIN MODEL TO A STRUCTURAL SCAN OF A BRAIN OF A PATIENT TO GENERATE A PATIENT-SPECIFIC 3D BRAIN REPRESENTATION REPRESENTING A THE BRAIN OF THE PATIENT 802

EXTRACT A PATIENT-SPECIFIC 3D BRAIN STRUCTURE REPRESENTATION FROM THE PATIENT-SPECIFIC 3D BRAIN REPRESENTATION 804

REGISTER FUNCTIONAL BRAIN ACTIVITY OF THE BRAIN OF THE PATIENT TO THE STRUCTURAL SCAN 806

MAP THE FUNCTIONAL BRAIN ACTIVITY TO THE EXTRACTED PATIENT-SPECIFIC 3D BRAIN STRUCTURE REPRESENTATION BASED ON THE FUNCTIONAL BRAIN ACTIVITY TO THE STRUCTURAL SCAN 808

IDENTIFY ONE OR MORE TARGET LOCATIONS ON THE PATIENT-SPECIFIC 3D BRAIN STRUCTURE REPRESENTATION BASED ON THE MAPPED FUNCTIONAL BRAIN ACTIVITY 810

EXPORT THE IDENTIFIED ONE OR MORE TARGET LOCATIONS AND MAPPED FUNCTIONAL BRAIN ACTIVITY TO A SURGICAL NAVIGATION SYSTEM 812

(51) Int. Cl.
　　*G06T 15/04*　　　　(2011.01)
　　*G06T 19/20*　　　　(2011.01)
(52) U.S. Cl.
　　CPC ... *A61B 2034/105* (2016.02); *A61B 2034/107*
　　　　　(2016.02); *G06T 2210/41* (2013.01); *G06T*
　　　　　　　　　　　　　　*2219/2004* (2013.01)

(56)　　　　　　　References Cited

U.S. PATENT DOCUMENTS

| | | | |
|---|---|---|---|
| 2016/0120457 A1* | 5/2016 | Wu ..................... | A61B 5/7435 |
| | | | 600/411 |
| 2016/0375248 A1* | 12/2016 | Carcieri .............. | A61N 1/3787 |
| | | | 607/59 |
| 2017/0032527 A1* | 2/2017 | Murthy ................. | H04N 23/20 |
| 2019/0159715 A1* | 5/2019 | Mishra Ramanathan .................. | |
| | | | A61B 5/377 |
| 2021/0264623 A1* | 8/2021 | Tandon ............... | A61B 5/4836 |
| 2022/0031226 A1* | 2/2022 | Zagorchev ............ | G16H 30/40 |
| 2023/0149091 A1* | 5/2023 | Cohen-Gadol ........ | G06T 15/08 |
| | | | 606/1 |
| 2024/0000509 A1* | 1/2024 | Xiao ..................... | A61B 90/39 |

* cited by examiner

800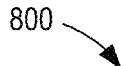

ADAPT A SHAPE-CONSTRAINED DEFORMABLE BRAIN MODEL TO A STRUCTURAL SCAN OF A BRAIN OF A PATIENT TO GENERATE A PATIENT-SPECIFIC 3D BRAIN REPRESENTATION REPRESENTING A THE BRAIN OF THE PATIENT 802

EXTRACT A PATIENT-SPECIFIC 3D BRAIN STRUCTURE REPRESENTATION FROM THE PATIENT-SPECIFIC 3D BRAIN REPRESENTATION 804

REGISTER FUNCTIONAL BRAIN ACTIVITY OF THE BRAIN OF THE PATIENT TO THE STRUCTURAL SCAN 806

MAP THE FUNCTIONAL BRAIN ACTIVITY TO THE EXTRACTED PATIENT-SPECIFIC 3D BRAIN STRUCTURE REPRESENTATION BASED ON THE FUNCTIONAL BRAIN ACTIVITY TO THE STRUCTURAL SCAN 808

IDENTIFY ONE OR MORE TARGET LOCATIONS ON THE PATIENT-SPECIFIC 3D BRAIN STRUCTURE REPRESENTATION BASED ON THE MAPPED FUNCTIONAL BRAIN ACTIVITY 810

EXPORT THE IDENTIFIED ONE OR MORE TARGET LOCATIONS AND MAPPED FUNCTIONAL BRAIN ACTIVITY TO A SURGICAL NAVIGATION SYSTEM 812

FIG. 8

AUTOMATIC NEUROSURGICAL TARGET AND ENTRY POINT IDENTIFICATION

TECHNICAL FIELD

The present disclosure relates generally to medical technologies, and more particularly, some examples relate to automated identification of neurosurgical target and entry points.

BACKGROUND

A brain-computer interface (BCI), sometimes called a brain-machine interface (BMI), is a communication pathway established between electrical activity of a brain and an external device, such as a computer or robotic limb. BCIs are often directed at acting on (e.g., researching, mapping, assisting, augmenting, repairing, and so on) human cognitive functions and/or sensory-motor functions. Implementations of BCIs can be achieved through non-invasive techniques (e.g., High Density Electroencephalography (HD-EEG), Magnetoencephalography (MEG), Electrooculography (EOG), Magnetic resonance imaging (MRI), etc.), partially invasive techniques (e.g., Electrocorticography (ECOG), endovascular, etc.), and invasive techniques (e.g., microelectrode array), depending on how close electrodes are to be implanted into brain tissue.

BRIEF DESCRIPTION OF THE DRAWINGS

The present disclosure, in accordance with one or more various examples, is described in detail with reference to the following figures. The figures are provided for purposes of illustration only and merely depict examples.

FIG. 8 depicts an example flow diagram that may be used to identify one or more target locations for device implantation with respect to a brain of a patient, in accordance with various examples of the presently disclosed technology.

Figure 1:
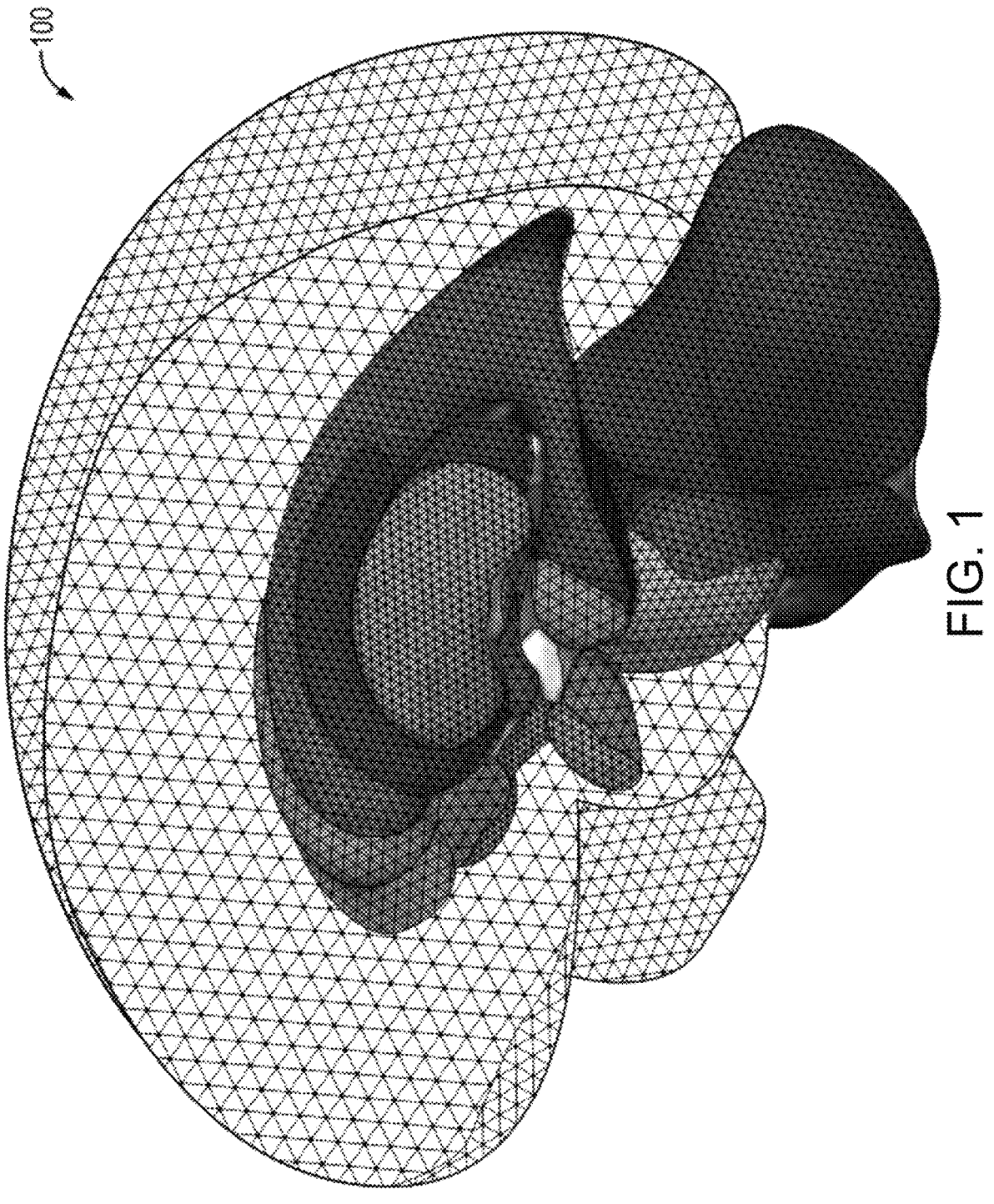
FIG. 1 depicts an example shape-constrained deformable brain model, in accordance with various examples of the presently disclosed technology.

The figures are not exhaustive and do not limit the present disclosure to the precise form disclosed.

DETAILED DESCRIPTION

Surgical planning prior to intervention can be an important aspect of neurosurgery, particularly in the field of BCI. Neurosurgeons generally try to plan out a target location for electrode implementation on a surface of the brain (e.g., the "cortical surface") and/or a surgical trajectory for subcortical placement within the brain before advancing a surgical instrument into a patient's brain. Such "pre-intervention evaluation" can assist to provide prospective target locations and surgical trajectories for implanting electrodes at regions of the brain that are active during performance of cognitive functions and/or sensory-motor functions to be acted upon by the BCI.

Generally, pre-intervention evaluation relies on manual and inexact evaluation techniques. In particular, neurosurgeons still largely rely on manual review of a series of images of a patient's brain (e.g., MRI or computerized tomography (CT) scans of the patient's brain) resliced orthogonal to one or more prospective surgical trajectories. Functional brain activity of a patient's brain in the form of a heatmap (such as that provided by a functional MRI or fMRI) are manually overlaid onto the series of images. From the overlaid functional brain activity, the neurosurgeon manually plans the prospective target location and/or surgical trajectory. Such manual review can be time-SMRH consuming, and can cause significant delays for complicated interventions that require multiple intra-operative adjustments. These delays can be especially harmful in interventions conducted under computerized tomography (CT) guidance because longer procedures expose the patient to additional radiation.

Further, pre-intervention evaluation can reduce patient trauma by identifying (and then avoiding) unsafe target locations and surgical trajectories prior to surgical insertion/advancement. In particular, the brain cortex (e.g., the outer layer of neural tissue of the human brain) is comprised of a numerous ridges called gyri, and fissures/grooves called sulci, which provide for a surface of the human brain (e.g., the "cortical surface") that is highly rugged/irregular. Furthermore, other anatomical structures, such as major blood vessels of the brain, lie at the cortical surface on gyri and/or within the sulci. Pre-intervention evaluation can take these anatomical structures into account when identifying a prospective target location and/or surgical trajectory. However, such considerations can further complicate the manual review.

The current manual approach to pre-intervention evaluation for brain surgeries also depends heavily on the expertise and judgment of an administering neurosurgeon—which presents drawbacks. In general, human decision-making can take longer than computer/automated decision-making. Also, human-decision making is also prone to errors which can potentially impact prospective surgical trajectory planning.

Against this backdrop, examples of the presently disclosed technology provide systems and methods for automatically identifying candidate target locations and candidate surgical trajectories using a functional brain activity scan mapped to patient-specific 3D brain structure representations generated from a structural scan of a patient's brain. According to various examples disclosed herein, functional brain activity can be obtained using a functional brain activity scan (e.g., an fMRI scan or any other scan modality capable of detecting and measuring neuronal activation in the patient's brain) that is registered (e.g., aligned) to a segmented structural scan used to generate the patient-specific 3D brain structure representations. A point-based correspondence between the structural scan and a patient-specific 3D brain structure representation can be leveraged to map the functional brain activity to the patient-specific 3D brain structure representation by assigning measures of neuronal activation from the functional brain activity scan to the patient-specific 3D brain structure representations. From the mapped functional activity, ideal and/or optimal target locations can be identified, which provides for individualized and optimal planning of targeting locations for interventions that incorporates both functional and structural information specific to the patient.

As alluded to above, the disclosed technology provides for accurate, automatic mapping of functional brain activity to a cortical surface of a human brain to assist with identification of one or more optimal target location on the cortical surface for device implementation and/or trajectory entry point identification. The shape and curvature of the cortical surface can be automatically calculated based on extracting the anatomical cortex from structural data of the patient. Functional brain activity can be mapped to patient-specific 3D brain structure representation and may be provided as a volumetric 3D activation area ("volume") that is mapped to a patient-specific 3D brain representation. An ideal candidate target location for device implementation (e.g., a target implantation point) can be identified from the mapped volume. In various examples, the mapped volume can be combined with additional information to refine the ideal candidate target location and identify an optimal candidate target location for a surgical intervention. The additional information may include, but is not limited to, device geometry which may be known in advance; radiologic scans; locations of anatomical structures, such as vasculature, sulci, and gyri, which may define hazard regions (e.g., no-go regions) to be avoided during surgery; and/or patient-specific constraint information provided by a user to define other hazard regions. The resulting mapped functional brain activity, ideal and/or optimal candidate target location, target surgical trajectory, etc. can be saved to the patient-specific 3D brain structure representation or as labeled objects on a structural scan. In some examples, this information can be exported to a surgical navigation or medical image storage system, a picture archiving and communication system (PACS) or the like, and provided to neurosurgeons to improve efficacy of surgical interventions.

As used herein, the term "intervention" refers to, but is not limited to, implantation, placement, angles of approach, trajectories, etc. for microelectrode arrays, electrocorticography grids and/or strips, electrodes, etc., and any other device that can be implemented as a BCI. Furthermore, this may be extended to any device or instrument used to perform a diagnostic and/or therapeutic neurosurgical procedure.

As used herein the phrase "target location" refers to a point located either on a cortical surface of the brain and/or at a sub-cortical region of the brain. A "target location" can refer to a target implantation point at which a device, such as a diagnostic and/or therapeutic device, can be implanted, such as on a cortical surface, on some other surface or structure of the brain, or on a sub-cortical surface or structure, depending on the implementation. A "target location" can also refer to a target entry point on the cortical surface of the brain at which an intervention may approach the brain for implanting a device at a target implantation point. A target surgical trajectory can be defined by a line that connects a target entry point to a target implantation point.

Examples of the disclosed technology provide a workflow for identifying optimal device implantation, through defining of optimal target locations and/or target surgical trajectories. The examples disclosed herein determine the optimal locations/trajectories using volume-to-surface mapping. For example, the disclosed technology adapts a shape-constrained deformable brain model to one or more structural scans of a patient's brain to generate a patient-specific 3D brain representation of the patient's brain. The patient-specific 3D mesh representation can be divided into a number of segments (e.g., sub-representations), each representing one or more structures of the patient's brain. A patient-specific 3D brain structure representation can be extracted from the segmented patient-specific 3D brain representation and meshed, where the patient-specific 3D brain structure representation is a target structure of the patient's brain for intervention. One or more functional brain activity scans can be registered (e.g., aligned) to the structural scan, which may be segmented into perspectives about a location of the functional brain activity on the brain. The functional brain activity can be mapped from the registered functional scans to the patient-specific 3D brain structure representation from the segmented structural scans. From the mapped functional brain activity, one or more ideal target locations can be defined on the patient-specific 3D brain structure representation. The one or more ideal target locations can then be refined (e.g., updated or otherwise augmented) to one or more optimal target locations based on other information, such as structural characteristics of the surface of the target location (e.g., curvatures), geometries of the intended device to be implemented, and additional patient-specific constraints (e.g., vasculature, hazard regions, etc.) that can define hazard regions. In various embodiments, the one or more optimal target locations and mapped functional brain activity can be exported to surgical navigation and/or image guidance systems.

In an illustrative example, the target structure is the cortical surface of the brain. In this example, a patient-specific 3D cortical ribbon representation can be extracted and meshed. Functional brain activity scans can be registered (e.g., aligned) to segmented structural scans and then mapped to the surface representation of the patient-specific 3D cortical ribbon. From the mapped functional brain activity data, ideal target locations can be defined based on the ideal target locations and additional information.

Examples of the presently disclosed technology can obtain the functional brain activity from functional brain activity scans and/or a functional atlas. Functional brain activity scans provide measures of brain activity (e.g., neuronal activation) on a position-basis within the brain of a patient. In the case of an fMRI scan, neuronal activation can be measured by detecting changes in blood flow at positions within the brain, which are coupled with neuronal activation. Namely, an fMRI scan detects increases in blood flow at positions of a volume of the brain when those positions (e.g., the volume) are in use (e.g., increased neuronal activation). An fMRI scan provides the measures of neuronal activation as a heatmap, where each position within the heatmap has a measure (e.g., value) of neuronal activation. While examples disclosed herein are described with reference to an fMRI scan, other functional brain activity scans are possible, such as, but not limited to, Electrical Source Imaging (ESI) from high density electro-encephalography (HD EEG), Magnetoencephalography (MEG), Positron Emission Tomography (PET), functional Near-Infrared Spectroscopy (fNIRS), or any other modality resulting in a volume of measures of neuronal activation.

In some example of the presently disclosed technology, registering the functional brain activity to the segmented structural scans can include aligning positions having neuronal activation in the functional brain activity scan to corresponding structure to the structure of the brain in the segmented structural scan.

Once aligned, the patient-specific 3D brain structure representation of the segmented structural scan can be leveraged to assign measures of neuronal activation to points of the patient-specific surface. For example, measures of neuronal activation at positions aligned to the structure in the segmented structural scan can be associated to the points of the segmented structural scan. Then the measures of neuronal activity can be assigned to points on the patient-specific 3D brain structure representation. As a result, the functional brain activity can be mapped to the patient-specific 3D brain structure representation, which can then be leveraged for identifying ideal and/or optimal target locations as described herein.

Examples of the presently disclosed technology will be described in greater detail in conjunction with the following figures.

It should be noted that the terms "optimize," "optimal" and the like as used herein can be used to mean making or achieving performance as effective or perfect as possible. However, as one of ordinary skill in the art reading this document will recognize, perfection cannot always be achieved. Accordingly, these terms can also encompass making or achieving performance as good or effective as possible or practical under the given circumstances, or making or achieving performance better than that which can be achieved with other settings or parameters.

FIG. 1 depicts an example shape-constrained deformable brain model 100, in accordance with various examples of the presently disclosed technology. Shape-constrained deformable brain model 100 may be a computerized 3D mesh representation of a generalized human brain (i.e., a non-patient-specific 3D representation of the human scalp, skull, brain, etc.) that preserves mesh vertex-based correspondences during mesh adaption to patient-specific data/scans using shape-constrained deformation. Shape-constrained deformable brain model 100 can be derived as an average/mean mesh from a set of training data.

As depicted, shape-constrained deformable brain model 100 comprises mesh elements and mesh vertices at the junctions of adjoining/adjacent mesh elements. Each mesh element of shape-constrained deformable brain model 100 may represent a different brain region. In the specific example of FIG. 1, the mesh elements of shape-constrained deformable brain model 100 comprise triangles, but in other examples mesh elements may comprise different shapes.

In general, a mesh may refer to a representation of a larger domain (e.g., a volume or surface) comprised of smaller discrete cells called mesh elements (e.g., mesh triangles or other shapes), and mesh vertices at the junctions of adjacent/adjoining mesh elements. Meshes can be used to compute solutions to equations across individual mesh elements, which then can be used to approximate solutions over the larger domain.

As depicted (and as will be discussed below), shape-constrained deformable brain model 100 may comprise individual 3D segments/sub-representations representing various structures of the brain (e.g., the cortical surface, sub-cortical structures such as the globus pallidus, the global pallidus internus (GPi), the putamen, the thalamus, etc.).

Figure 2:
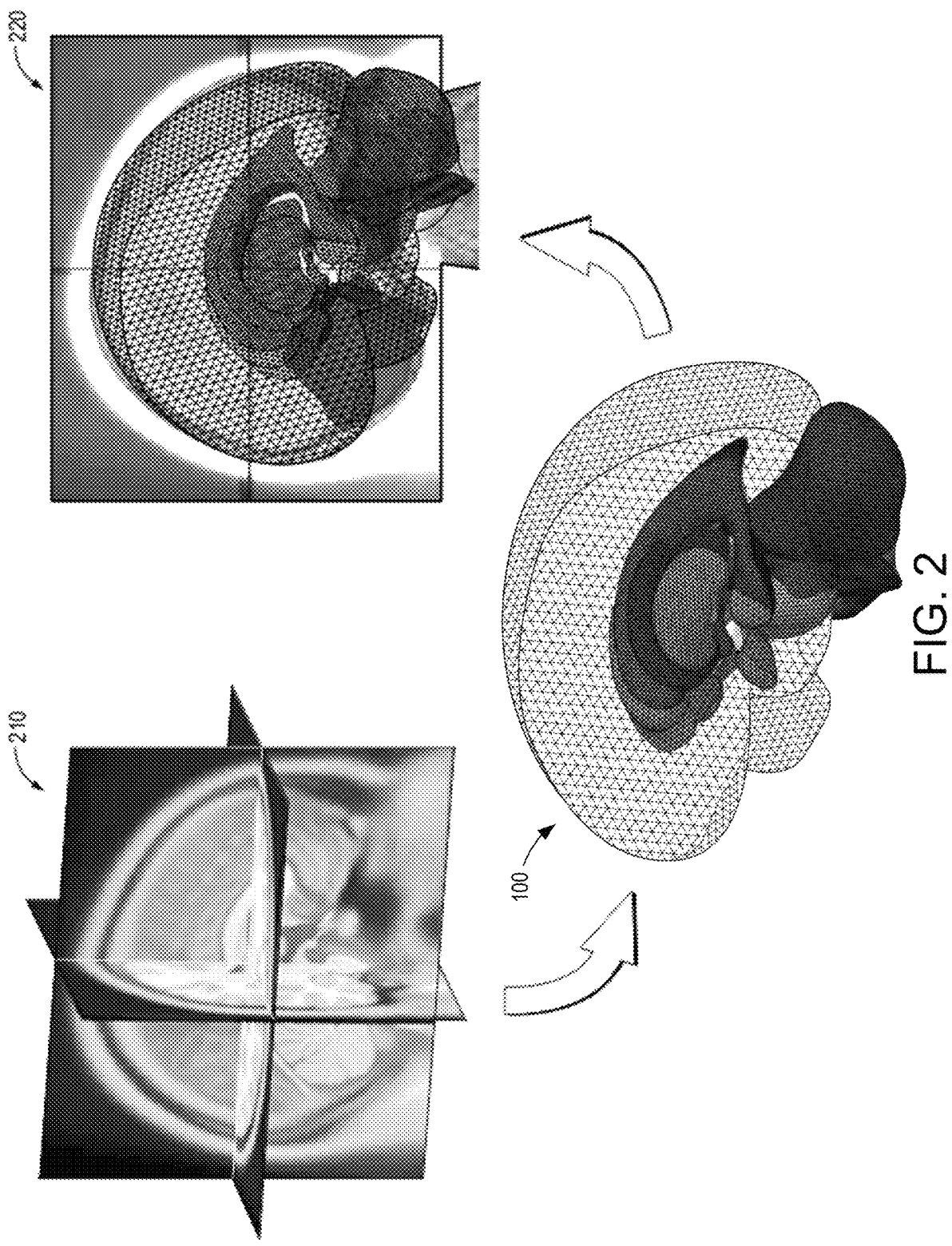
FIG. 2 depicts an example adaption of a shape-constrained deformable brain model to a scan of a patient's brain to generate a patient-specific 3D mesh brain representation, in accordance with examples of the presently disclosed technology.

FIG. 2 depicts an example adaption of shape-constrained deformable brain model 100 to a scan 210 of a patient's brain to generate a patient-specific 3D mesh brain representation 220 and a dense deformation field that transforms a mean shape of shape-constrained deformable brain model 100 to the scan 210 of the patient's brain, in accordance with examples of the presently disclosed technology. The shape-constrained deformable brain model 100 can be adapted to structural scans, such as volumetric structural scans, of the patient's brain (e.g., MRI scans, CT scans, etc.) to generate patient-specific 3D brain representations. As depicted in FIG. 2, patient-specific 3D mesh brain representation 220 may comprise individual 3D mesh sub-representations/segments representing individual brain structures of the patient (e.g., patient-specific 3D brain structure mesh representations). The patient-specific 3D brain structure mesh representations may represent the various brain structures (e.g., cortex structures, sub-cortical structures, etc.) of the patient's brain.

As alluded to above, shape-constrained deformable brain model 100 may be a computerized 3D mesh representation of a generalized human brain (e.g., a non-patient-specific 3D representation of the human brain) that preserves mesh vertex-based correspondences during mesh adaption to patient-specific data/scans using shape-constrained deformation. Namely, the process of mesh adaption generates a dense deformation field that transforms voxels from the coordinate space of the shape-constrained deformable brain model 100 (e.g., the shape-constrained deformable brain model 100 coordinate space) to a coordinate space of an imaging system (such as but not limited to Digital Imaging and Communications in Medicine (DICOM) standard interchange protocol) of scan 210 (e.g., the scan 210 coordinate space). The dense deformation field can leverage shape-constrained deformation to constrain deformation to an apriori derived mean mesh (e.g., shape-constrained deformable brain model 100). The dense deformation field can use a penalty term estimated from the mean mesh (e.g., estimated from shape-constrained deformable brain model 100) that prevents topological changes during mesh adaptation, which may be an iterative process. Segmentation (e.g., generation of individual/segmented patient-specific 3D brain structure mesh representations, such as a patient-specific 3D brain structure mesh brain representation representing the cortical surface) may gradually deform the mean mesh (e.g., gradually deform shape-constrained deformable brain model 100) to match the patient-specific scan (e.g., scan 210). In other words, shape may be constrained to the mean mesh (e.g., constrained to shape-constrained deformable brain model 100), which can grow or shrink without morphing into a different shape.

Where patient-specific 3D brain representation 220 is a voxel-based representation, examples can segment (e.g., extract) individual 3D brain structure mesh representations by applying a marching cubes algorithm to the 3D brain representation 220. In an illustrative example, a 3D cortical surface mesh representation may be a 3D boundary surface of the 3D representation for the brain structure. In certain cases, examples can generate the 3D cortical surface mesh representation by applying the marching cubes algorithm to the 3D representation for the brain structure.

Through the above-described adaptation, mesh vertex-based correspondences can be preserved between mesh vertices of shape-constrained deformable brain model 100 and mesh vertices of the patient-specific 3D brain structure mesh representations 220. Accordingly, a functional brain activity scan can be mapped to patient-specific 3D brain structure mesh representations using volume to surface mapping. Leveraging this adaption/transformation feature (e.g., preservation of mesh vertex-based correspondences), examples can define candidate target device placements for a surgical procedure by leveraging (1) mesh vertex-based correspondences between a patient-specific 3D brain structure mesh representation and functional brain activity data; and (2) correspondence with additional information, such as structural characteristics of the patient-specific 3D brain structure mesh representation, geometries of the device to be implemented during the surgical procedure, and additional patient-specific constraints (e.g., vasculature, hazard regions, etc.).

Figure 3:
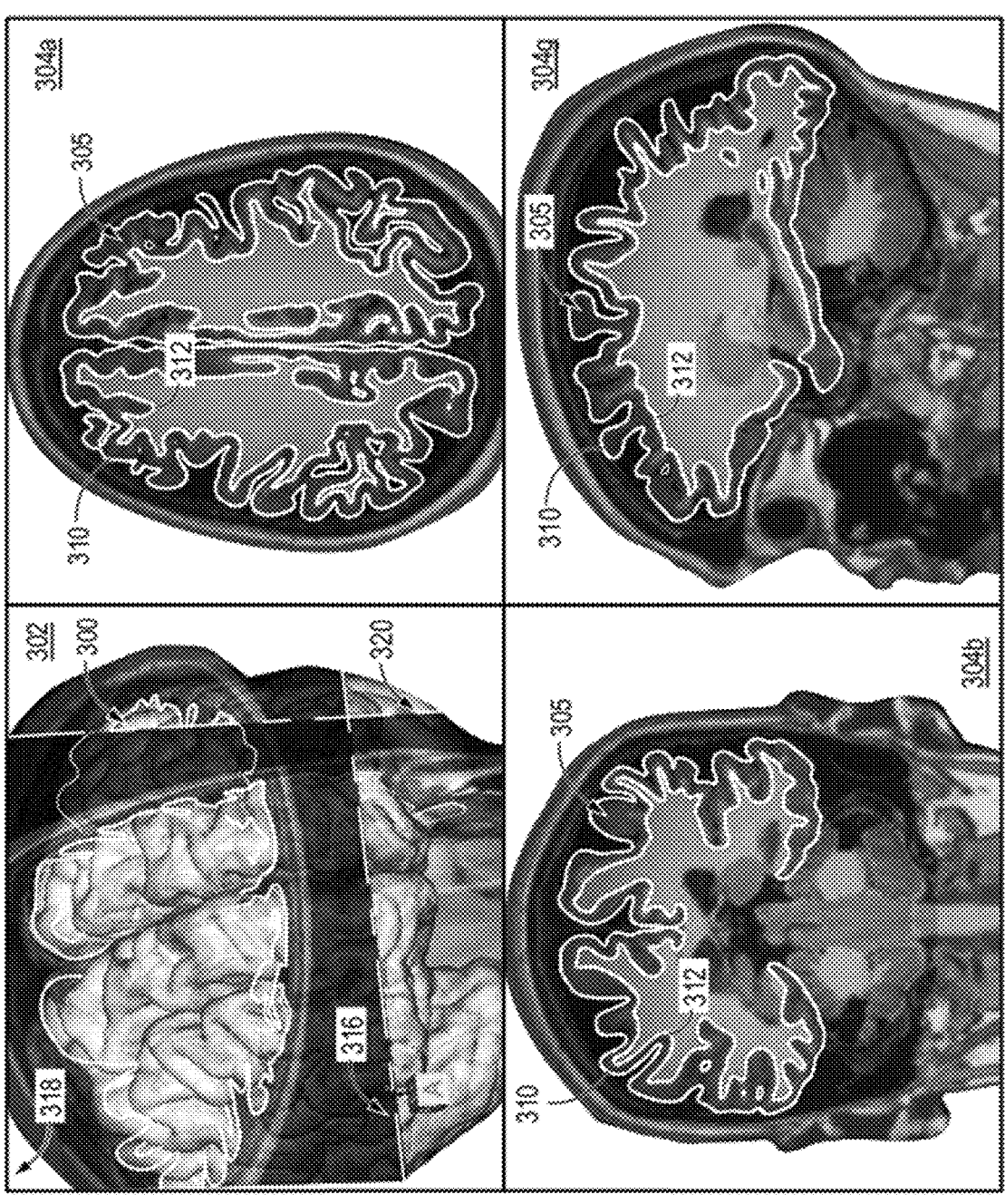
FIG. 3 depicts an example of a 3D brain structure extracted from a patient-specific 3D brain representation to generate a patient-specific 3D brain structure mesh representation, in accordance with an example of the presently disclosed technology.

FIG. 3 depicts an example of a 3D brain structure extracted from a patient-specific 3D brain representation to generate a patient-specific 3D brain structure mesh representation 300, in accordance with an example of the presently disclosed technology. Here, the patient-specific 3D brain structure mesh representation 300 (which may also be referred to as a patient-specific 3D brain structure representation) may be an individual segment/sub-representation of patient-specific 3D mesh brain representation 220, which represents a patient's cortical ribbon in this example. As such, the patient-specific 3D brain structure mesh representation 300 may be referred to a patient-specific 3D cortical ribbon mesh representation in this example. As alluded to above, the cortical surface is a common target for BCI procedures, although other cortex structures and/or sub-cortical brain structures may be targeted as well.

FIG. 3 depicts patient-specific 3D cortical ribbon mesh representation 300 as a perspective view in image 302. Image 302 also depicts coronal plane 318, transverse plane 316, and a sagittal plane 320, which provide cross-sectional planes of patient-specific 3D cortical ribbon mesh representation. Cross-sectional planar views of patient-specific 3D cortical ribbon mesh representation 300 are shown in images 304a-304c for coronal plane 318, transverse plane 316, and a sagittal plane 320, respectively. Images 304a-304c depict a structural scan segmented by the coronal plane 316, transverse plane 318, and a sagittal plane 320 to provide each respective view. Thus, images 304a-304c may collectively represent a segmented volumetric structural scan 304 (e.g., a structural MRI scan, or CT scan, or the like).

Examples generate the patient-specific 3D cortical surface mesh representation 300 using the segmented structural scan 304 of a patient's brain. The patient-specific 3D cortical surface mesh representation 300 may represent the cortex of the patient. Examples can generate the 3D cortical surface mesh representation 300 from imaging data (e.g., images 304a-304c) of any structure of the patient's brain obtained by the structural scan using the techniques described in conjunction with FIGS. 1 and 2. For instance, examples can first generate a patient-specific 3D brain representation by adapting a generalized shape-constrained deformable brain model 100 to the imaging data of the patient's brain.

The generated patient-specific 3D brain representation can include individual 3D mesh sub-representations/segments for the brain structures of the patient. A cortical ribbon

305 can be defined by an inner boundary (or surface) and an outer boundary (or cortical surface). The individual 3D mesh sub-representations/segments can be extracted from the patient-specific 3D brain representation. For example, the segmented structural scan can be comprised of points (or voxels) that delineate a structure of the brain from the entirety of the brain. In the example of FIG. 3, the cortical ribbon (or more particularly, the cortical surface and inner surface) can be delineated from the other structures of the brain in the segmented structural scan using the points (or voxels) that delineate a cortical ribbon from these other structures.

A point-based correspondence between a patient-specific 3D brain representation and the segmented structural scan 304 can be maintained. For example, where the segmented structural scan is a voxel-based representation, examples can segment (e.g., extract) a 3D cortical surface mesh representation 310 by applying a marching cubes algorithm to the cortical surface in the segmented structural scan. As another example, a 3D inner surface mesh representation 312 can be extracted by applying a marching cubes algorithm to the 3D brain structure representation of the inner surface. Together, the 3D cortical surface mesh representation 310 and 3D inner surface mesh representation 312 can be used to define a 3D cortical ribbon mesh representation 305.

As described in conjunction with FIGS. 1 and 2, in certain cases the 3D brain representation may comprise mesh elements and mesh vertices at the junctions of adjoining/adjacent mesh elements and the 3D cortical surface mesh representation may similarly comprise mesh elements and mesh vertices. These 3D meshes may preserve the point-based correspondences between mesh vertices of the generalized 3D brain representation and mesh vertices of the patient-specific 3D brain structure mesh representations. These point-based correspondences can be used to identify the various brain structures of the patient. Additionally, these 3D meshes may preserve the point-based correspondences between voxels of the segmented structural scan 304 and mesh vertices of the generalized 3D brain representation and/or mesh vertices of the patient-specific 3D brain structure mesh representations, or patient-specific 3D brain structure mesh representations of different subjects.

Figure 4:
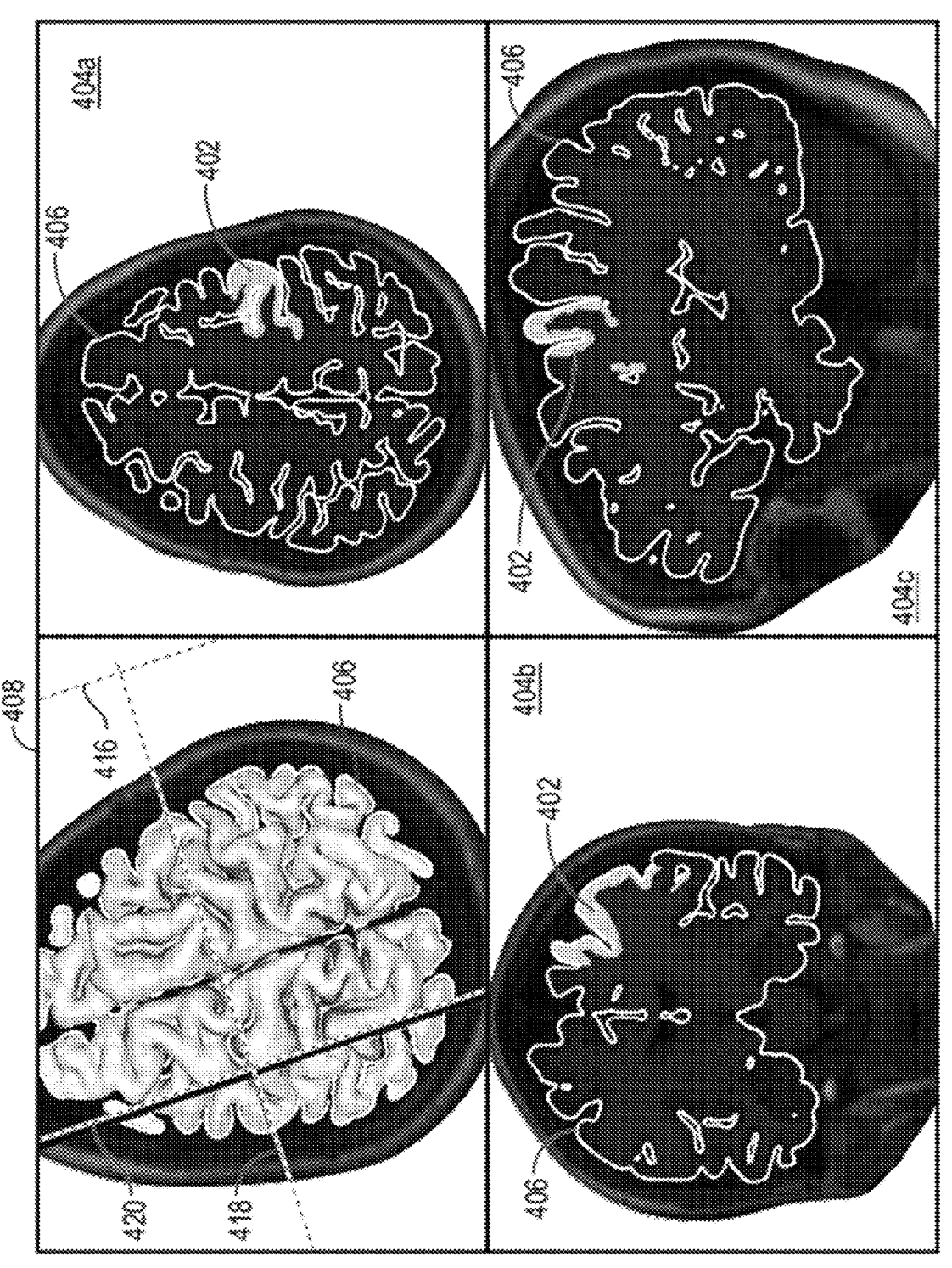
FIG. 4 depicts an example of functional brain activity of a patient's brain registered to a segmented structural scan of the patient's brain along with a patient-specific 3D brain structure mesh representation, in accordance with an example of the presently disclosed technology.

FIG. 4 depicts an example of functional brain activity 402 of a patient's brain registered to a segmented structural scan 404 of the patient's brain along with a patient-specific 3D cortical surface mesh representation 406 of the patient's cortical surface, in accordance with an example of the presently disclosed technology. FIG. 4 depicts the patient-specific 3D cortical surface mesh representation 406 as a top down view in image 408, along with transverse plane 416, coronal plane 418, and a sagittal plane 420 that are representative of views for segmented images 404a-404c of a segmented structural scan 404 with respect to the patient-specific 3D cortical surface mesh representation 406. In each segmented image 404a-c, the patient-specific 3D cortical surface mesh representation 406 is shown overlaid on the segmented structural scan 404 along with the functional brain activity 402.

As alluded to above, the functional brain activity 402 may be obtained from functional brain activity scans (e.g., fMRI, ESI from HD EEG, MEG, PET, fNIRS, functional atlas, or any other modality resulting in a 3D volume of functional brain activity). Functional brain activity scans provide measures of neuronal activation on a point- or position-basis within the brain of a patient. The functional brain activity scan provides the measures of neuronal activation as one or more volumetric activity regions (or "volumes") heatmaps, where each position within the heatmap corresponds to a position (or point) in the brain having neuronal activation and a measure (e.g., value) of neuronal activation shown as a color/shade gradient relative to other positions (or points) of the heatmap. Thus, each position (or point) of the heatmap can be associated with a measure of neuronal activation.

The functional brain activity, as one or more volumetric activity areas, is registered to the segmented structural scan. For example, positions having neuronal activation in the functional brain activity can be aligned to corresponding structures in the segmented structural scan 404. Namely, the positions in the functional brain activity scan may be provided as voxels collectively defining the volumetric activity region (e.g., in a coordinate space of the functional brain activity scan), and these voxels can be aligned with voxels from a coordinate space of the segmented structural scan 404, which provides a correspondence between the functional brain activity 402 and the segmented structural scan 404. With this correspondence, measures (e.g., values) of neuronal activation of each voxel (e.g., point or position) in the functional activity scan can be associated with voxels of the segmented structural scan 404 that are aligned to the voxels of the functional brain activity 402.

Figure 5:
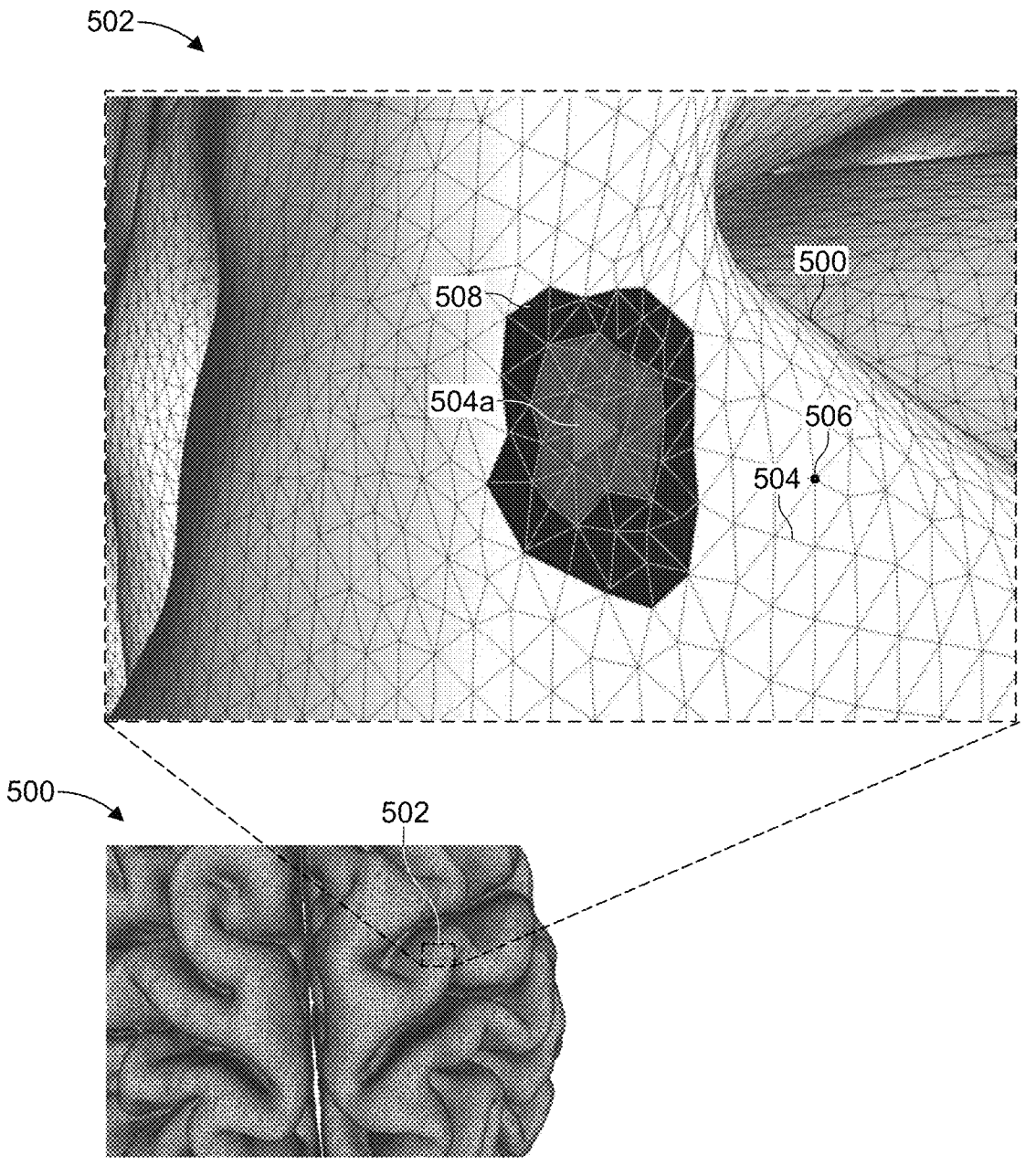
FIG. 5 depicts an example patient-specific 3D brain structure mesh representation having a functional brain activity mapped thereto, in accordance with an example of the presently disclosed technology.

FIG. 5 depicts an example patient-specific 3D cortical surface mesh representation 500 having a functional brain activity 508 mapped to one or more mesh elements 504 of the patient-specific 3D cortical surface mesh representation 500, in accordance an example of the presently disclosed technology. The patient-specific 3D cortical surface mesh representation 500 can be generated using the techniques described above in conjunction with FIGS. 1-3. As described above, patient-specific 3D cortical surface mesh representation 500 comprises mesh elements 504 (a single mesh element being labeled as representative of mesh elements) and mesh vertices 506 (a single mesh vertex being labeled as representative of mesh vertices) at the junctions of adjoining/adjacent mesh elements. As shown in the example implementation, mesh elements may comprise triangles; however, mesh elements may comprise different shapes.

As described above, the segmented structural scan and the patient-specific 3D brain structure representation can be leveraged to map the functional brain activity, registered to the segmented structural scan, to the patient-specific 3D brain structure representation. This can be utilized to assign measures of neuronal activation to points of the patient-specific 3D brain structure representation. For example, measures of neuronal activity can be assigned to points on the patient-specific 3D brain structure representation based on the segmented structural scan.

FIG. 5 depicts an example of this volume to surface mapping. Particularly, in the zoomed-in region 502, functional brain activity 508 is mapped to one or more mesh elements 504 of the patient-specific 3D cortical surface mesh representation 500. That is, the functional brain activity registered to the segment structural scan is mapped to mesh elements 504 as functional brain activity 508.

Where patient-specific 3D cortical surface mesh representation 500 is a voxel-based representation, examples voxels from the coordinate space of the segmented structural scan (e.g., segmented structural scan 404) can be mapped to the patient-specific 3D cortical surface mesh representation 500. Each voxel in the coordinate space of the segmented structural scan can be associated (or otherwise assigned) with a measure of neuronal activation according to the alignment therebetween (e.g., as described in connection with FIG. 4). The measures of neuronal activation can then be assigned to mesh elements 504 of the patient-specific 3D cortical surface mesh representation 500 based on the voxels in the coordinate space of the segmented structural scan associated with the measures of neuronal activation and the mesh elements 504 of the of the patient-specific 3D cortical surface mesh representation 500.

Examples herein can map the functional brain activity 508 to the mesh elements, along with an aggregation of measures of neuronal activation previously assigned to each mesh element and a count of a total number of voxels mapped to each respective mesh element. In an illustrative example, for each voxel in the segmented structural scan, a closest mesh element 504 can be located from patient-specific 3D cortical surface mesh representation 500 based on geometric distance. The voxel is mapped to the located, closest mesh element 504. Next, the functional brain activity associated with the voxel is assigned to the located, closest mesh element 504 by adding the measure of neuronal activation to an aggregation of measures of neuronal activation previously assigned to the located mesh element. For example, functional brain activity can be assigned as follows:

$$\text{new\_activity}_i = \text{old\_activity}_i + \text{Activity Measure} \qquad \text{Eq. 1}$$

where Activity Measure represents the measure of neuronal activation for a given voxel (e.g., a voxel under consideration) in the coordinate space of the segmented structural scan; $\text{old\_activity}_i$ represents an aggregation (e.g., summation) of all measures of neuronal activation previously assigned to the $i^{th}$ mesh element (e.g., in the case of a first instance, $\text{old\_activity}_i$ would be 0); and i represents an $i^{th}$ mesh element, which is the located, closest mesh element to the voxel under consideration.

For each mesh element, a count of voxels in the coordinate space of the segmented structural scan mapped to a given mesh element 504, based on the correspondence, can be updated. Namely, where a mesh element 504 is located as the closest mesh element to a voxel in the coordinate space of the segmented structural scan, the count is incremented by an integer (e.g., 1). As additional voxels are mapped to the mesh element 504, the count is updated by one for each voxel.

Once all voxels in the coordinate space of the segmented structural scan are mapped to mesh elements 504, the aggregation of measures of neuronal activation assigned to a given mesh element 504 can be divided by the final, total count of mapped voxels. Namely, new_activity for each mesh element 504 is divided by the total number of voxels assigned to the respective mesh element 504. Thus, the functional brain activity can be normalized across the mesh elements 504.

As a result, the functional brain activity is mapped to the closest mesh elements of the patient-specific 3D cortical surface mesh representation 500, as shown in FIG. 5. In the illustrative example of FIG. 5, functional brain activity 508 is represented as a heatmap, where a mesh element 504a is assigned the highest aggregate measure of neuronal activation (e.g., highest value in the aggregate). In some implementations, mesh element 504a may represent an ideal target implantation point or ideal entry point for an intervention, such as implanting a BCI.

While the above example is described with respect to the cortical surface, examples disclosed herein are not intended to be limited to only the outer surface. For example, the implementations disclosed here can be extended to an inner surface of the cortical ribbon, where a patient-specific 3D inner surface mesh representation is generated and functional brain activity is mapped to mesh elements of the patient-specific 3D inner surface representation. Similarly, functional brain activity can be mapped to surfaces of sub-cortical structures by generating patient-specific 3D brain structure mesh representation and mapping functional brain activity thereto.

Examples can determine an optimal target location for device implementation based on the mapping of functional brain activity to the patient-specific 3D cortical surface mesh representation. For example, an optimal target location can be determined by thresholding mesh elements based on functional brain activity mapped thereto. That is, a threshold limit of functional brain activity may be set, and mesh elements assigned functional brain activity greater than the threshold limit may be used to define an optimal location. As another example, optimal target locations can be determined based on estimating a principal curvature for the mesh elements mapped with the functional brain activity. In yet another example, optimal target locations can be determined by selecting a center of mass of mesh elements with principle curvature above a threshold limit as a candidate target location. That is, for example, one or more mesh elements having a highest functional brain activity assigned thereto (e.g., the center of mass) and a principle curvature that is larger than a curvature threshold may be used to define an optimal candidate target location. In some examples, the functional brain activity scan may identify multiple volumetric activity areas, each of which can be mapped to a patient-specific 3D cortical surface mesh representation. In this case, an optimal target location may be determined as an intersection and/or overlap between the two or more multiple volumetric activity areas. An optimal target location may be determined using any one of the above techniques, as well as any combination thereof.

In some examples, additional information on anatomical structures located within the vicinity of mapped functional brain activity can be used to refine a candidate optimal target location. Anatomical structures may define "no-go" or hazard brain regions where a target location or a surgical trajectory could result in trauma to the patient by damaging anatomical structures or allowing for unsafe trajectories that could cause deflection of the device when inserted into the brain. These regions represent areas of the brain to be avoided during surgery. Defining these hazard regions can reduce patient trauma by identifying (and then avoiding) unsafe target locations or surgical trajectories by defining no-go regions to be avoided during surgery.

In one example, one or more 3D hazard regions representations can be generated using a structural scan of the patient's brain. Anatomical structures can be identified from structural scans, or other co-registered radiologic images (e.g., CT, MRA, etc.). For example, anatomical structures such as vasculature, sulci, and other structures can be identified from scans of a patient's brain. Here, the techniques described above in connection with FIGS. 1 and 2 for generating a patient-specific 3D brain structure mesh representations can be extended to generate one or more patient-specific 3D hazard region representation of the anatomical structure(s) identified in the scan. As such, the one or more patient-specific 3D hazard region representations can be provided as a mesh comprising mesh elements and mesh vertices, as described above.

In another example, hazard regions can be identified based on user input identifying such hazard regions and then marked on patient-specific 3D brain structure representations. These hazard regions can be set in advance and automatically generated on structural scans or automatically marked on the patient-specific 3D brain structure representation as hazard regions in the patient-specific 3D brain structure representation. Using this information, the presently disclosed technology can refine an identified target location to automatically determine an optimal target location that is based on both the target location and hazard regions to be avoided in view of a known geometry of the device to be placed/implanted into the brain structure of the patient (e.g., intracortical microelectrode array, sub-dural ECOG arrays, etc.).

Examples disclosed herein can utilize other constraints, along with ideal or optimal candidate target locations to define an optimal angle of intervention approach. For example, other constraints can include information on a desired angle of approach to the patient's cortical surface, which can be supplied to the disclosed technology to define an optimal angle. As another example, information on an angle for implanting a device can be used to determine an optimal angle of approach.

Figure 6:
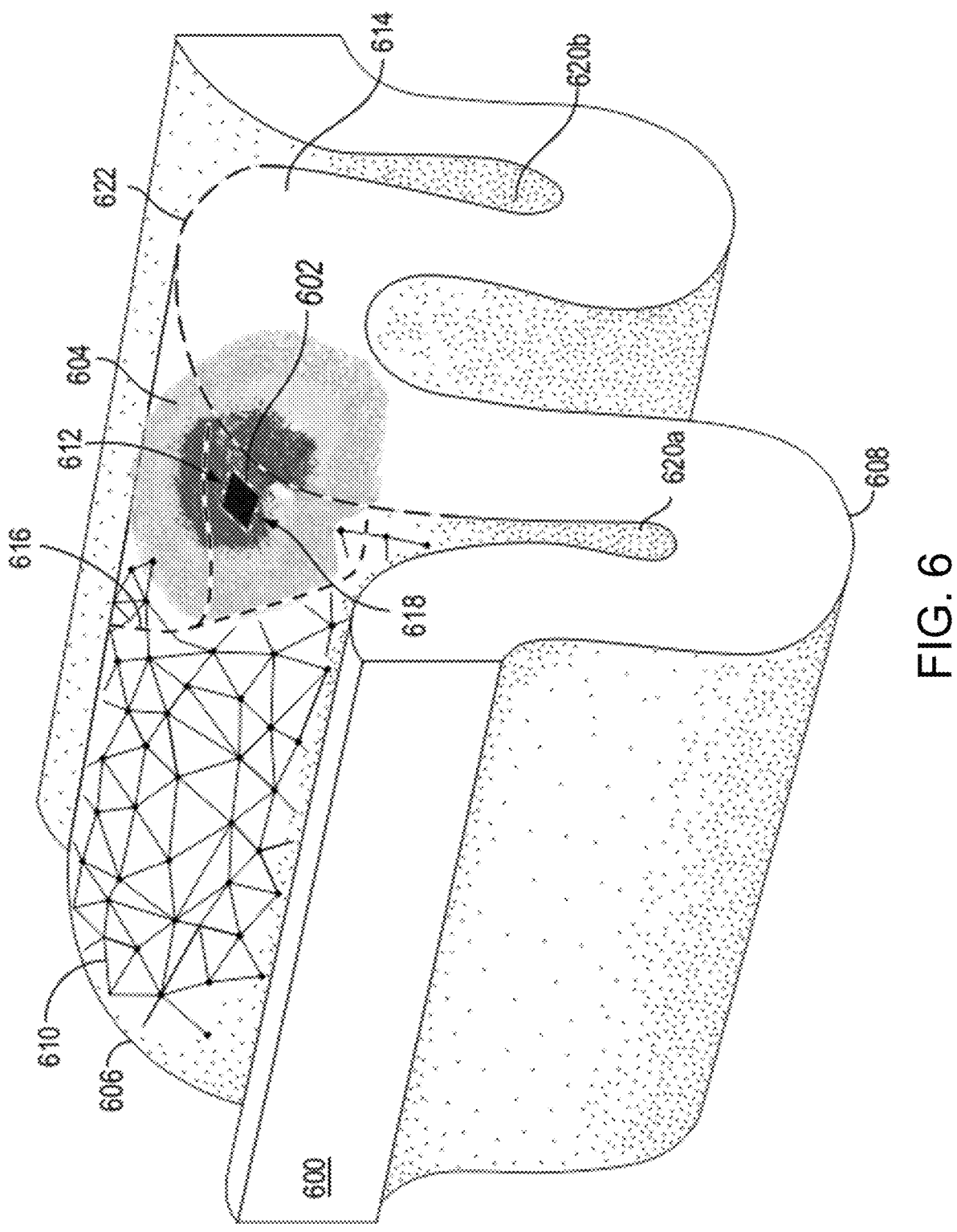
FIG. 6 depicts an example for defining an optimal candidate target location on a patient-specific 3D brain structure mesh representation, in accordance with an example of the presently disclosed technology.

FIG. 6 depicts an example for defining an optimal candidate target location on a patient-specific 3D brain structure mesh representation 600 based on a geometry of a device 602 and functional brain activity 604 mapped to patient-specific 3D brain structure mesh representation 600, in accordance with an example of the presently disclosed technology. Particularly, FIG. 6 depicts a zoomed-in portion of the patient-specific 3D brain structure mesh representation 600, which is provided as a patient-specific 3D cortical ribbon mesh representation 600. While the cortical ribbon is represented in this example, other brain structures, such as sub-cortical brain structures, may be represented as well. The patient-specific 3D cortical ribbon mesh representation 600 can be generated from a structural scan of the patient's brain using the techniques described in conjunction with FIGS. 1-3.

The generated patient-specific 3D cortical ribbon mesh representation 600 can include individual 3D mesh sub-representations/segments. For example, patient-specific 3D cortical ribbon mesh representation 600 can be comprised by patient-specific 3D cortical surface mesh representation 606 and patient-specific 3D inner surface mesh representation 608. Each of which may comprise a mesh of mesh elements and mesh vertices. FIG. 6 depicts mesh 610 of patient-specific 3D cortical surface mesh representation 606 for illustrative purposes. While not shown in FIG. 6, patient-specific 3D cortical ribbon mesh representation 600 and/or patient-specific 3D inner surface mesh representation 608 can comprise similar meshes.

The functional brain activity 604 can be mapped to the patient-specific 3D cortical ribbon mesh representation 600 based on a functional brain activity scan, as described in conjunction with FIGS. 4 and 5. As a result, the functional brain activity 604 is mapped to mesh elements of the patient-specific 3D cortical ribbon mesh representation 600 as a heatmap having an ideal target location 612 located at a point of the highest functional brain activity (e.g., the center of the heatmap in this example). In this example, the functional brain activity 604 is on a gyrus 614 of the patient-specific 3D cortical ribbon mesh representation 600, between adjacent sulci 620a and 620b. Here, an optimal target location for device 602 can be determined based on calculating a principle curvature 622 of the patient-specific 3D cortical ribbon mesh representation 600 where the functional brain activity 604 is located (e.g., the gyrus 614 in this example) based on the mesh elements to which the functional brain activity 604 is assigned. From the calculated curvature 622 and geometry of the device 602, an optimal target location for device 602 can be determined to ensure that device 602 is optimally positioned with respect to the volumetric area of the functional brain activity 604.

As described above, additional information contained within the structural scan can include anatomical structures, which can be used to define hazard regions for implementation. The optimal target location can be further refined by defining one or more of the identified anatomical structures as hazard regions for device 602. In the example of FIG. 6, a structural scan can be used to identify vasculature (e.g., blood vessel 616) and sulci 620*a* and 620*b*, which may be provided as respective meshes. As shown in FIG. 6, the ideal location 612 in view of the dimensions of the device 602 would result in the device 602 being dangerously close to the blood vessel 616. Thus, to avoid trauma to the patient, the technology disclosed herein can mark the blood vessel 616 as a hazard region and shift the target location from the ideal target location 612 to the optimal target location 618, thereby avoiding damage to the blood vessel 616 during implementation of device 602. The distance of the shift in target location can be based on the geometry of device 602, as well as the functional brain activity 604 and other identified anatomical structures depending on the particular application.

As alluded to above, the presently disclosed technology is not limited to the structures of the cerebral cortex but can be extended to the entirety of the human brain (e.g., sub-cortical structures). As such, in an example implementation, functional brain activity identified at anywhere in the brain from a functional brain activity scan can be mapped to any surface of a patient-specific 3D brain structure representation and/or any segmented patient-specific 3D brain structure representation, regardless of whether the patient-specific 3D brain structure representation represents cerebral cortex structures or sub-cortical structures. For example, deep structures and nuclei, such as those within the basal ganglia and midbrain, can be represented by segmented patient-specific 3D brain structure representation and functional activity mapped thereto in a manner substantially similar to that described connection with FIGS. 1-6.

In some examples, functional brain activity can be mapped to circuits, or the intersection of circuits, within the human brain. The circuits and/or intersections can be identified through tractography techniques and functional brain activity mapped to the identified structures as described above.

Functional brain activity that is mapped to the deeper, sub-cortical structures (including circuits in sub-cortical regions) may be used to define target locations. The target locations can then be used to inform a surgical trajectory angle of approach for implanting of electrodes, which have contacts along the length of the electrode with a set geometry. An optimal entry point for implantation may be identified using the techniques described herein, which can be combined with the target location to define a trajectory. Such implementations may be of particular value in deep brain stimulation (DBS) applications, as DBS moves beyond just motor function and into psychiatry-based interventions (e.g., "connectomic DBS"). In this case, a mapped functional brain activity could be used to provide concordance between structural and functional information of the brain, including tractography, to refine and optimize one or more target locations (e.g., the target implantation point and/or entry point) and/or surgical trajectory.

As alluded to above, optimal entry points identified on the cortical surface identified as described in connection with FIGS. 1-6 can be combined with optimal target locations in sub-cortical regions described above. A line formed between the two points may be used to define a surgical trajectory. Additional information along the length of the optimal surgical trajectory and within a mapped functional brain activity at the target location (e.g., vasculature, sulci, ventricles, hazard regions, etc.) could be defined automatically and/or by the user. By considering the additional information along with the defined surgical trajectory, an optimal surgical trajectory can be defined that accounts for the additional information to augment (if necessary) the defined surgical trajectory. For example, a defined surgical trajectory can be augmented to avoid hazard regions at the cortical surface and/or deeper within the sub-cortical region. Similarly, an optimal surgical trajectory may be defined so to intercept a "go," or non-hazard, region. Augmenting the surgical trajectory may include augmenting the position of the target implantation point, the position of the entry point, adjusting an angle of entry, etc.

As some illustrative examples, consider the following. An optimal trajectory may be defined along a long axis of a mapped functional brain activity, as opposed to on the cortical ribbon. This may enable an optimal placement of an electrode of having a set geometry such that the electrode is implanted along the long axis to maximize a length of the interface between electrical activity of the brain and the electrode. As another example, an optimal trajectory may be determined to allow electrode contacts to be placed along a length of an overlap of multiple volumes of mapped functional brain activity, with an intersection of multiple brain circuits identified from tractography. In yet another example, using the intersection/overlap of multiple brain circuits to define a target functional brain activity, an optimal trajectory can be automatically defined along a long axis of the target functional brain activity, thereby optimizing an entry point and avoiding hazard regions along the trajectory. In another example, placement of a thin-film ECOG grid or strip of device geometry can be optimized using structural and functional information as disclosed herein.

Figure 7A:
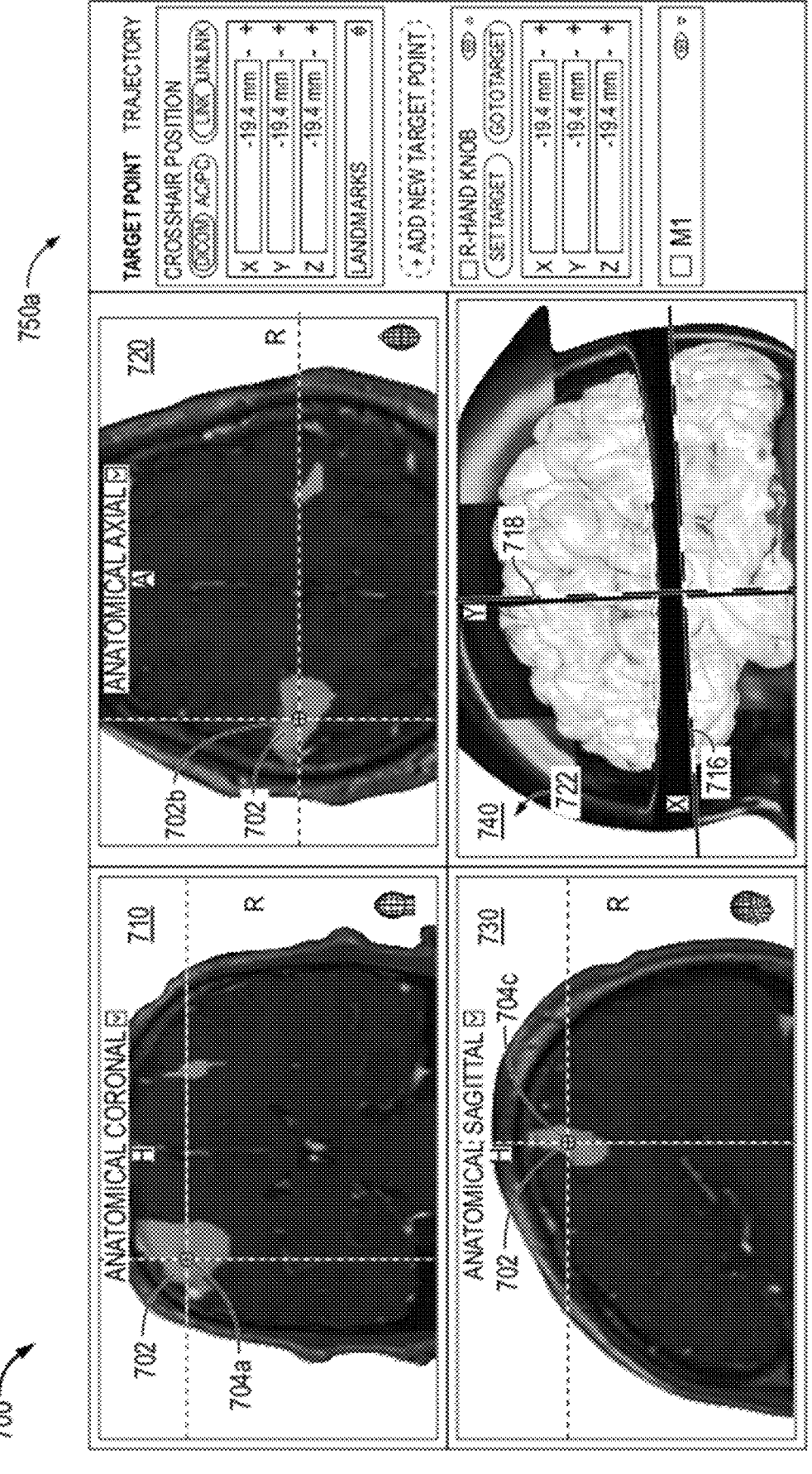
FIG. 7A depict screen shots of an example graphical user interface (GUI) generated by a target location system according to examples of the presently disclosed technology FIG. 7B depict screen shots of an example graphical user interface (GUI) generated by a trajectory identification system according to examples of the presently disclosed technology.
Figure 7B:
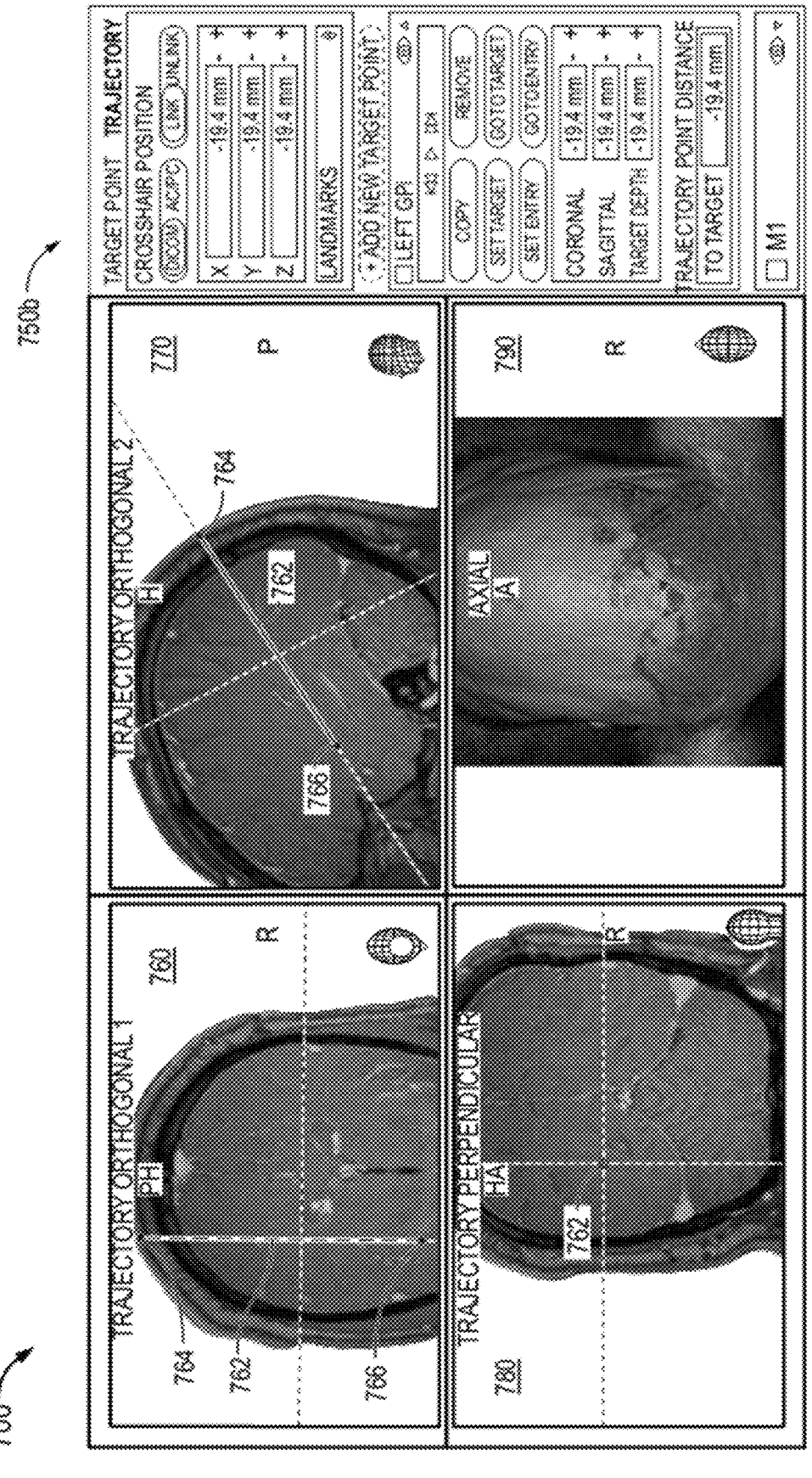
Figure 9:
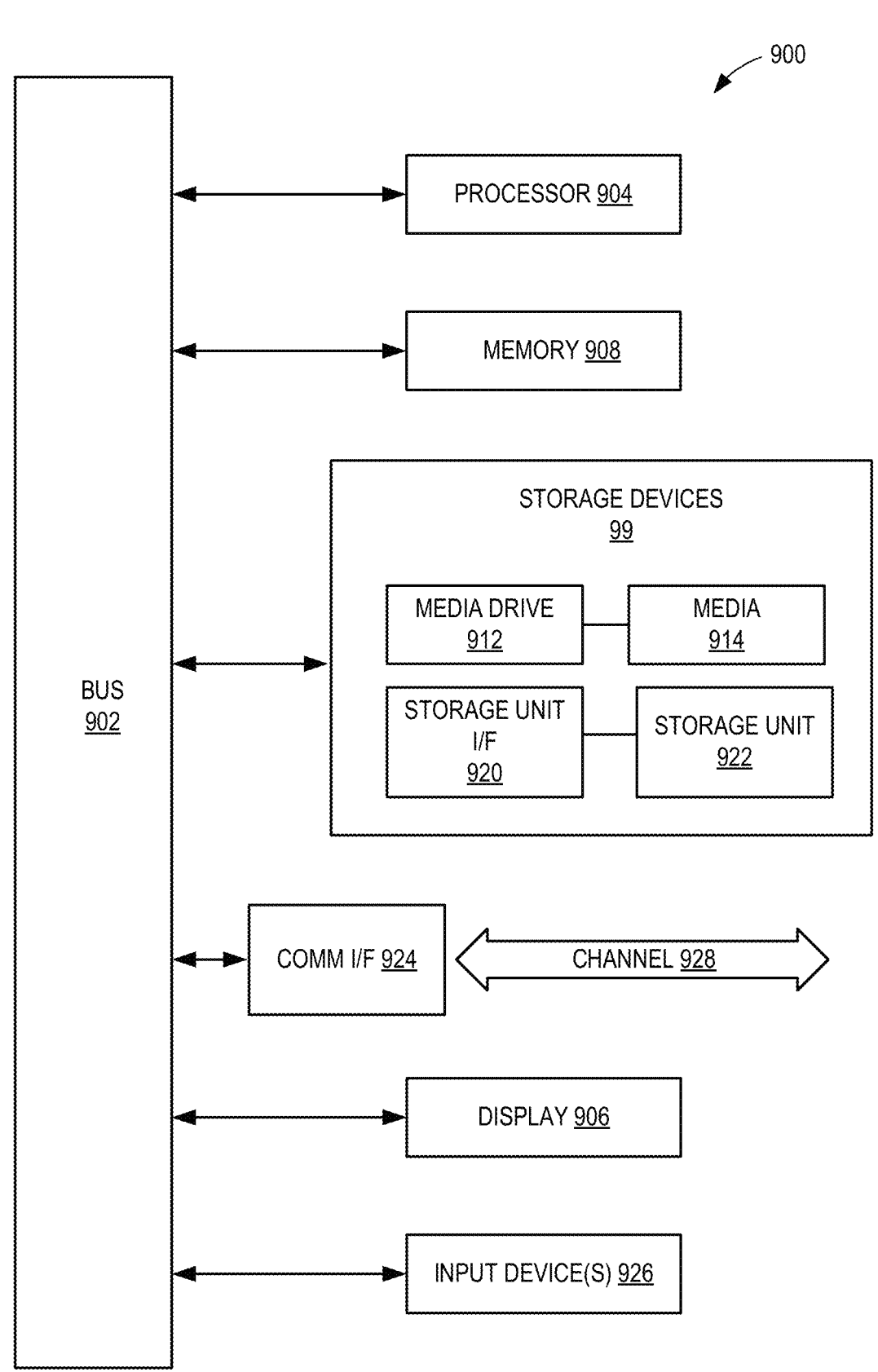
FIG. 9 is an example computing component that may be used to implement various features of examples described in the present disclosure.

FIGS. 7A and 7B depict screenshots of an example graphical user interface (GUI) 700 generated by a target location/trajectory identification system according to examples of the presently disclosed technology. The target location/trajectory identification system may be implemented as, for example, a computing system (e.g., a personal computer, server, laptop, tablet, smart phone, or the like). For example, the target location/trajectory identification system computing component is shown in FIG. 9. The GUI 700 may be provided as instructions stored in a memory that, when executed by a processor, cause the processor to generate one or more display viewports that include graphical visual representations of one or more viewports of a user interface, menus, icons, controls, tabs, etc., presented on a display (e.g., a monitor, TV screen, display screen of a mobile device, display screen of a tablet or portable computing device, etc.). The GUI 700 may be used for visually reviewing and confirming optimal candidate target locations and/or surgical trajectories that are identified by the target location/trajectory identification system. The GUI 700 may also provide user controls that can be used to augment the target location/trajectory identified by the system according to user inputs into the system.

The GUI 700 shown in FIG. 7A graphically displays a first plurality of viewports (or panes) 710-730 that present a visualization of the segmented structural scan overlaid with the functional brain activity 702 from a functional brain activity scan. Additionally, each viewport 710-730 includes a crosshair 704a-704c representative of the optimal target location, which in this example may be a target implantation point in the cortical surface. Crosshair 704a-704c represents an intersection point of the three planes (e.g., coronal, transverse and sagittal planes). Another viewport 740 displays the patient-specific 3D brain structure mesh representation 706 (e.g., the patient-specific 3D cortical surface mesh representation in this example) and coronal plane 718, transverse plane 716, and a sagittal plane 722, which correspond to viewports 710, 720, and 730, respectively. The patient-specific 3D brain structure mesh representation 706 may be generated as described above in connection with FIGS. 1-3 and the optimal target location identified as described above in connection with FIGS. 4-6.

The GUI 700 shown in FIG. 7B graphically displays a second plurality of viewports 760-780 that present a visualization of the structural scan overlaid with a trajectory 762 defined by an entry point 764 and a target implantation point 766. While not shown in FIG. 7B, functional brain activity can be displayed on the structural scans, as shown in FIG. 7A. Viewport 760 displays a segment of the structural scan rendered along a plane that is orthogonal to the trajectory 762, viewport 770 displays a segment of the structural scan rendered along a plane that is orthogonal to the trajectory 762 and orthogonal to the view shown in viewport 760. Viewport 780 displays a segment of the structural scan rendered along a plane that is perpendicular to the trajectory 762. Each of the entry point 764 and the target implantation point 766 may be identified as optimal target locations as described above in connection with FIGS. 4-6. Identified in this way, together the entry point 764 and target implantation point 766 define an optimal surgical trajectory. Another viewport 790 displays a three-dimensional rendered image of a patient's head.

The GUI 700 can also generate a user interaction panel 750. User interaction panel 750 provides a variety of functionality to enable a user to interact with the software to review, plan, augment, and confirm the optimal target locations or trajectories. The user interaction panel 750 can include sub-panels, shown as target location sub-panel 750a (FIG. 7A) and a trajectory sub-panel 750b (FIG. 7B). Sub-panels may be provided for interacting with the optimal target location as a target implantation point, or optimal target locations as an entry point on the cortical surface and a target implantation point collectively defining a target surgical trajectory.

FIG. 8 depicts an example flow diagram that may be used to identify one or more target locations for device implantation with respect to a brain of a patient, in accordance with various examples of the presently disclosed technology. FIG. 8 illustrates a process 800 that may be implemented as instructions, for example, stored in a memory, that when executed by one or more processors perform, or cause to be performed, the operations of process 800.

At operation 802, examples adapt a shape-constrained deformable brain model to a structural scan of a brain of a patient to generate a patient-specific 3D brain representation of the patient's brain. This operation may be performed in the same/similar manner as described in conjunction FIGS. 1-2.

At operation 804, examples extract a patient-specific 3D brain structure representation from the patient-specific 3D brain representation. The patient-specific 3D brain structure representation represents a structure of the brain of the patient. This operation may be performed in the same/similar manner as described in conjunction FIG. 3.

At operation 806, examples register functional brain activity of the brain of the patient to the structural scan. This operation may be performed in the same/similar manner as described in conjunction FIG. 4.

At operation 808, examples map the functional brain activity to the extracted patient-specific 3D brain structure representation based on the functional brain activity to the structural scan. This operation may be performed in the same/similar manner as described in conjunction FIG. 5.

At operation 810, examples identify one or more target locations on the patient-specific 3D brain structure representation based on the mapped functional brain activity. This operation may be performed in the same/similar manner as described in conjunction FIGS. 5 and 6.

At optional operation 812 (as indicated by the dashed line), examples can export the identified one or more target locations and mapped functional brain activity to a surgical navigation or medical image storage system. As described above, this information can be exported to a surgical navigation or medical image storage system and provided to neurosurgeons to improve efficacy of surgical interventions. In some examples, operation 812 can convert the information from a proprietary data structure or protocol to a non-proprietary or standard protocol, such as the Digital Imaging and Communications in Medicine (DICOM) standard interchange protocol. The information can then be exported to PACS (or other image management systems) or other external systems for consumption via the standard protocol, for example, through a wireless or wired communication interface.

As used herein, the terms circuit and component might describe a given unit of functionality that can be performed in accordance with one or more examples of the present application. As used herein, a component might be implemented utilizing any form of hardware, software, or a combination thereof. For example, one or more processors, controllers, ASICs, PLAS, PALs, CPLDs, FPGAs, logical components, software routines, or other mechanisms might be implemented to make up a component. Various components described herein may be implemented as discrete components or described functions and features can be shared in part or in total among one or more components. In other words, as would be apparent to one of ordinary skill in the art after reading this description, the various features and functionality described herein may be implemented in any given application. They can be implemented in one or more separate or shared components in various combinations and permutations. Although various features or functional elements may be individually described or claimed as separate components, it should be understood that these features/ functionality can be shared among one or more common software and hardware elements. Such a description shall not require or imply that separate hardware or software components are used to implement such features or functionality.

Where components are implemented in whole or in part using software, these software elements can be implemented to operate with a computing or processing component capable of carrying out the functionality described with respect thereto. One such example computing component is shown in FIG. 9. Various examples are described in terms of this example computing component 900. After reading this description, it will become apparent to a person skilled in the relevant art how to implement the application using other computing components or architectures.

Referring now to FIG. 9, computing component 900 may represent, for example, computing or processing capabilities found within a self-adjusting display, desktop, laptop, notebook, and tablet computers. They may be found in hand-held computing devices (tablets, PDA's, smart phones, cell phones, palmtops, etc.). They may be found in workstations or other devices with displays, servers, or any other type of special-purpose or general-purpose computing devices as may be desirable or appropriate for a given application or environment. Computing component 900 might also represent computing capabilities embedded within or otherwise available to a given device. For example, a computing component might be found in other electronic devices, such as, for example, portable computing devices, and other electronic devices that might include some form of processing capability.

Computing component 900 might include, for example, one or more processors, controllers, control components, or other processing devices. Processor 904 might be implemented using a general-purpose or special-purpose processing engine, such as, for example, a microprocessor, controller, or other control logic. Processor 904 may be connected to a bus 902. However, any communication medium can be used to facilitate interaction with other components of computing component 900 or to communicate externally.

Computing component 900 might also include one or more memory components, simply referred to herein as main memory 908. For example, random access memory (RAM), or other dynamic memory, might be used for storing information and instructions to be executed by processor 904. Main memory 908 might also be used for storing temporary variables or other intermediate information during execution of instructions to be executed by processor 904. Computing component 900 might likewise include a read-only memory ("ROM") or other static storage device coupled to bus 902 for storing static information and instructions for processor 904.

The computing component 900 might also include one or more various forms of information storage mechanism 910, which might include, for example, a media drive 912 and a storage unit interface 920. The media drive 912 might include a drive or other mechanism to support fixed or removable storage media 914. For example, a hard disk drive, a solid-state drive, a magnetic tape drive, an optical drive, a compact disc (CD) or digital video disc (DVD) drive (R or RW), or other removable or fixed media drive might be provided. Storage media 914 might include, for example, a hard disk, an integrated circuit assembly, magnetic tape, a cartridge, an optical disk, a CD or DVD. Storage media 914 may be any other fixed or removable medium that is read by, written to, or accessed by media drive 912. As these examples illustrate, the storage media 914 can include a computer usable storage medium having stored therein computer software or data.

In alternative examples, information storage mechanism 910 might include other similar instrumentalities for allowing computer programs or other instructions or data to be loaded into computing component 900. Such instrumentalities might include, for example, a fixed or removable storage unit 922 and an interface 920. Examples of such storage units 922 and interfaces 920 can include a program cartridge and cartridge interface, a removable memory (for example, a flash memory or other removable memory component), and a memory slot. Other examples may include a PCMCIA slot and card, and other fixed or removable storage units 922 and interfaces 920 that allow software and data to be transferred from storage unit 922 to computing component 900.

Computing component 900 might also include a communications interface 924. Communications interface 924 might be used to allow software and data to be transferred between computing component 900 and external devices. Examples of communications interface 924 might include a modem or softmodem, a network interface (such as Ethernet, network interface card, IEEE 802.XX, TCP/IP socket, or other interface). Other examples include a communications port (such as, for example, a USB port, IR port, RS232 port Bluetooth® interface, or other port), or other communications interface. Software/data transferred via communications interface 924 may be carried on signals, which can be electronic, electromagnetic (which includes optical), or other signals capable of being exchanged by a given communications interface 924. These signals might be provided to communications interface 924 via a channel 928. Channel 928 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media. Such media may be, e.g., memory 908, storage unit 922, media 914, and channel 928. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 900 to perform features or functions of the present application as discussed herein.

The computing component 900 may be coupled via bus 902 to a display 906, such as a liquid crystal display (LCD) (or touch screen), for displaying information to a computer user. An input device 926, including alphanumeric and other keys, is coupled to bus 902 for communicating information and command selections to processor 904. Another type of user input device is cursor control, such as a mouse, a trackball, or cursor direction keys for communicating direction information and command selections to processor 904 and for controlling cursor movement on display 906. In some embodiments, the same direction information and command selections as cursor control may be implemented via receiving touches on a touch screen without a cursor.

The computing component 900 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

It should be understood that the various features, aspects, and functionality described in one or more of the individual examples are not limited in their applicability to the particular example with which they are described. Instead, they can be applied, alone or in various combinations, to one or more other examples, whether or not such examples are described and whether or not such features are presented as being a part of a described example. Thus, the breadth and scope of the present application should not be limited by any of the above-described exemplary examples.

Terms and phrases used in this document, and variations thereof, unless otherwise expressly stated, should be construed as open-ended as opposed to limiting. As examples of the foregoing, the term "including" should be read as meaning "including, without limitation" or the like. The term "example" is used to provide exemplary instances of the item in discussion, not an exhaustive or limiting list thereof. The terms "a" or "an" should be read as meaning "at least one," "one or more," or the like; and adjectives such as "conventional," "traditional," "normal," "standard," "known," or terms of similar meaning should not be construed as limiting the item described to a given time period or to an item available as of a given time. Instead, they should be read to encompass conventional, traditional, normal, or standard technologies that may be available or known now or at any time in the future. Where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to," or other like phrases in some instances shall not be read to mean that the narrower case is intended or required in instances where such broadening phrases may be absent. The use of the term "component" does not imply that the aspects or functionality described or claimed as part of the component are all configured in a common package. Indeed, any or all of the various aspects of a component, whether control logic or other components, can be combined in a single package or separately maintained and can further be distributed in multiple groupings or packages or across multiple locations.

Additionally, the various examples set forth herein are described in terms of exemplary block diagrams, flow charts, and other illustrations. As will become apparent to one of ordinary skill in the art after reading this document, the illustrated examples and their various alternatives can be implemented without confinement to the illustrated examples. For example, block diagrams and their accompanying description should not be construed as mandating a particular architecture or configuration.

What is claimed is:

1. A method, comprising:
adapting a shape-constrained deformable brain model to a structural scan of a patient's brain to generate a patient-specific 3D brain representation of the patient's brain;
extracting a patient-specific 3D brain structure representation from the patient-specific 3D brain representation, the patient-specific 3D brain structure representation comprising a mesh formed of mesh elements representing a structure of the patient's brain;
aligning measures of neuronal activation at positions within the structure of the patient's brain to voxels of the structural scan delineating the structure of the patient's brain;
mapping the measures of neuronal activation to the mesh elements of the extracted patient-specific 3D brain structure representation based on correspondence between the voxels associated with the measures of neuronal activation and the mesh elements of the patient-specific 3D brain structure representation; and
identifying one or more target locations on the patient-specific 3D brain structure representation based on the mapped measures of neuronal activation.

2. The method of claim 1, the method further comprising:
for each voxel of the structural scan,
locating a closest mesh element from the patient-specific 3D brain structure representation to the voxel to map the voxel to the located mesh element;
mapping the measure of neuronal activation to the located mesh element by adding the measure of neuronal activation to an aggregation of measures of neuronal activation previously mapped to the located mesh element; and
incrementing a count of voxels previously mapped to the located mesh element based on the voxel; and
for each mesh element, dividing the aggregation of measures of neuronal activation for the mesh element by the count of voxels mapped to the mesh element.

3. The method of claim 1, wherein identifying one or more target locations on the patient-specific 3D brain structure representation based on the mapped measures of neuronal activation is based on one or more of: thresholding mesh elements based on the measures of neuronal activation mapped to the mesh elements, estimating a curvature for the structure based on the mesh elements, and selecting a center of mass of the mesh elements with a curvature above a curvature threshold.

4. The method of claim 1, further comprising:
generating one or more hazard region representations based on at least one of the structural scan of the patient's brain or a user input, each hazard region representation representing a hazard region of the patient's brain to be avoided during surgery,
wherein the one or more target locations on the patient-specific 3D brain structure representation are identified based on the one or more hazard region representations.

5. The method of claim 1, wherein the one or more target locations on the patient-specific 3D brain structure representation are identified based on a geometry of a device to be surgically implanted on the structure of the patient's brain represented by the patient-specific 3D brain structure representation.

6. The method of claim 1, further comprising:
exporting the identified one or more target locations and mapped measures of neuronal activation to at least one of: a surgical navigation system or a medical image storage system.

7. The method of claim 1, wherein the patient-specific 3D brain structure representation represents a cortical surface of the patient's brain, wherein the one or more target locations comprise a target implantation point on the cortical surface.

8. The method of claim 1, wherein the patient-specific 3D brain structure representation represents a sub-cortical structure of the patient's brain, wherein the one or more target locations comprises a target implantation point on the sub-cortical structure.

9. The method of claim 8, wherein the identified one or more target locations comprises a target entry point located on a cortical surface of the patient's brain, wherein a surgical trajectory is defined based on the target implantation point and the target entry point.

10. The method of claim 1, wherein extracting the patient-specific 3D brain structure representation from the patient-specific 3D brain representation comprises:
applying a marching cubes algorithm to the voxels of the structural scan delineating the structure of the patient's brain to generate mesh elements and mesh vertices that collectively provide the patient-specific 3D brain structure representation.

11. A system comprising:

one or more processing resources; and non-transitory computer-readable memory, coupled to the one or more processing resources, having stored therein instructions that when executed by the one or more processing resources cause the system to perform a method comprising:

adapting a shape-constrained deformable brain model to a structural scan of a patient's brain to generate a patient-specific 3D brain representation of the patient's brain;

extracting a patient-specific 3D brain structure representation from the patient-specific 3D brain representation, the patient-specific 3D brain structure representation comprising a mesh formed of mesh elements representing a structure of the patient's brain;

aligning measures of neuronal activation at positions within the structure of the patient's brain to voxels of the structural scan delineating the structure of the patient's brain;

mapping the measures of neuronal activation to the mesh elements of the extracted patient-specific 3D brain structure representation based on correspondence between the voxels associated with the measures of neuronal activation and the mesh elements of the patient-specific 3D brain structure representation; and identifying one or more target locations on the patient-specific 3D brain structure representation based on the mapped measures of neuronal activation.

12. The system of claim 11, the method further comprising:

generating one or more hazard region representations based on at least one of the structural scan of the the patient's brain or a user input, each hazard region representation representing a hazard region of the patient's brain to be avoided during surgery, wherein the one or more target locations on the patient-specific 3D brain structure representation are identified based on the one or more hazard region representations.

13. The system of claim 11, wherein the one or more target locations on the patient-specific 3D brain structure representation are identified based on a geometry of a device to be surgically implanted on the structure of the patient's brain represented by the patient-specific 3D brain structure representation.

14. The system of claim 11, the method further comprising:

exporting the identified one or more target locations and mapped measures of neuronal activation to at least one of: a surgical navigation system or a medical image storage system.

15. The system of claim 11, wherein the patient-specific 3D brain structure representation represents a cortical surface of the patient's brain, wherein the one or more target locations comprise a target implantation point on the cortical surface.

16. The system of claim 11, wherein extracting the patient-specific 3D brain structure representation from the patient-specific 3D brain representation comprises:

applying a marching cubes algorithm to the voxels of the structural scan delineating the structure of the patient's brain to generate mesh elements and mesh vertices that collectively provide the patient-specific 3D brain structure representation.

17. Non-transitory computer-readable storage memory including instructions that, when executed by at least one processor of a computing system, cause the computing system to perform a method comprising:

adapting a shape-constrained deformable brain model to a structural scan of a patient's brain to generate a patient-specific 3D brain representation of the patient's brain;

extracting a patient-specific 3D brain structure representation from the patient-specific 3D brain representation, the patient-specific 3D brain structure representation comprising a mesh formed of mesh elements representing a structure of the patient's brain;

aligning measures of neuronal activation at positions within the structure of the patient's brain to voxels of the structural scan delineating the structure of the patient's brain;

mapping the measures of neuronal activation to the mesh elements of the extracted patient-specific 3D brain structure representation based on correspondence between the voxels associated with the measures of neuronal activation and the mesh elements of the patient-specific 3D brain structure representation; and identifying one or more target locations on the patient-specific 3D brain structure representation based on the mapped measures of neuronal activation.

18. The non-transitory computer-readable storage memory of claim 17, wherein identifying one or more target locations on the patient-specific 3D brain structure representation based on the mapped measures of neuronal activation is based on one or more of: thresholding mesh elements based on the measures of neuronal activation to the mesh elements, estimating a curvature for the structure based on the mesh elements, and selecting a center of mass of the mesh elements with a curvature above a curvature threshold.

19. The non-transitory computer-readable storage memory of claim 17, wherein the one or more target locations on the patient-specific 3D brain structure representation are identified based on a geometry of a device to be surgically implanted on the structure of the patient's brain represented by the patient-specific 3D brain structure representation.

20. The non-transitory computer-readable storage memory of claim 17, wherein the method further comprises exporting the identified one or more target locations and mapped measures of neuronal activation to at least one of: a surgical navigation system or a medical image storage system.

* * * * *